(12) United States Patent
Richardson et al.

(10) Patent No.: US 9,119,600 B2
(45) Date of Patent: Sep. 1, 2015

(54) DEVICE AND METHODS FOR RENAL NERVE MODULATION MONITORING

(71) Applicant: BOSTON SCIENTIFIC SCIMED, INC., Maple Grove, MN (US)

(72) Inventors: Leonard B. Richardson, Brooklyn Park, MN (US); Scott R. Smith, Chaska, MN (US); Mark L. Jenson, Greenfield, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 257 days.

(21) Appl. No.: 13/678,306

(22) Filed: Nov. 15, 2012

(65) Prior Publication Data

US 2013/0123778 A1    May 16, 2013

Related U.S. Application Data

(60) Provisional application No. 61/560,026, filed on Nov. 15, 2011.

(51) Int. Cl.
| | |
|---|---|
| *A61B 19/00* | (2006.01) |
| *A61B 18/14* | (2006.01) |
| A61B 18/16 | (2006.01) |
| A61B 17/32 | (2006.01) |
| A61B 18/18 | (2006.01) |

(Continued)

(52) U.S. Cl.
CPC .............. *A61B 19/00* (2013.01); *A61B 18/1492* (2013.01); *A61B 17/320068* (2013.01); *A61B 18/1815* (2013.01); *A61B 18/20* (2013.01); *A61B 19/54* (2013.01); *A61B 2018/00029* (2013.01); *A61B 2018/00285* (2013.01); *A61B 2018/00446* (2013.01); *A61B 2018/00511* (2013.01); *A61B 2018/00547* (2013.01); *A61B 2018/00577* (2013.01); *A61B 2018/00815* (2013.01); *A61B 2018/00821* (2013.01); *A61B 2018/00875* (2013.01); *A61B 2018/167* (2013.01)

(58) Field of Classification Search
USPC ........................................................ 607/9, 37
See application file for complete search history.

(56) References Cited

U.S. PATENT DOCUMENTS

| | | |
|---|---|---|
| 164,184 A | 6/1875 | Kiddee |
| 1,167,014 A | 1/1916 | O'Brien |

(Continued)

FOREIGN PATENT DOCUMENTS

| | | |
|---|---|---|
| DE | 10038737 A1 | 2/2002 |
| EP | 1053720 A1 | 11/2000 |

(Continued)

OTHER PUBLICATIONS

Van Den Berg, "Light echoes image the human body," OLE, Oct. 2001, p. 35-37.

(Continued)

*Primary Examiner* — Nicole F Lavert
(74) *Attorney, Agent, or Firm* — Seager, Tufte & Wickhem, LLC

(57) ABSTRACT

Systems and methods for monitoring and performing tissue modulation are disclosed. An example system may include an elongate shaft having a distal end region and a proximal end and having at least one modulation element and one sensing electrode disposed adjacent to the distal end region. The sensing electrode may be used to determine and monitor changes in tissue adjacent to the modulation element.

14 Claims, 7 Drawing Sheets

(51) Int. Cl.
    *A61B 18/20*    (2006.01)
    *A61B 18/00*    (2006.01)

(56)            References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |

(56) References Cited

U.S. PATENT DOCUMENTS

| | | |
|---|---|---|
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy-Chutorian et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |

(56) References Cited

U.S. PATENT DOCUMENTS

| | | |
|---|---|---|
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |

(56) References Cited

U.S. PATENT DOCUMENTS

| | | |
|---|---|---|
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Leatham et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |

(56) References Cited

U.S. PATENT DOCUMENTS

| | | |
|---|---|---|
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |

(56) References Cited

U.S. PATENT DOCUMENTS

| | | |
|---|---|---|
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,727,229 B2 | 6/2010 | He et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |

(56) References Cited

U.S. PATENT DOCUMENTS

| | | | |
|---|---|---|---|
| 7,846,160 | B2 | 12/2010 | Payne et al. |
| 7,846,172 | B2 | 12/2010 | Makower |
| 7,849,860 | B2 | 12/2010 | Makower et al. |
| 7,850,685 | B2 | 12/2010 | Kunis et al. |
| 7,853,333 | B2 | 12/2010 | Demarais |
| 7,854,734 | B2 | 12/2010 | Biggs et al. |
| 7,857,756 | B2 | 12/2010 | Warren et al. |
| 7,862,565 | B2 | 1/2011 | Eder et al. |
| 7,863,897 | B2 | 1/2011 | Slocum, Jr. et al. |
| 7,869,854 | B2 | 1/2011 | Shachar et al. |
| 7,873,417 | B2 | 1/2011 | Demarais et al. |
| 7,887,538 | B2 | 2/2011 | Bleich et al. |
| 7,894,905 | B2 | 2/2011 | Pless et al. |
| 7,896,873 | B2 | 3/2011 | Hiller et al. |
| 7,901,400 | B2 | 3/2011 | Wham et al. |
| 7,901,402 | B2 | 3/2011 | Jones et al. |
| 7,901,420 | B2 | 3/2011 | Dunn |
| 7,905,862 | B2 | 3/2011 | Sampson |
| 7,918,850 | B2 | 4/2011 | Govari et al. |
| 7,927,370 | B2 | 4/2011 | Webler et al. |
| 7,937,143 | B2 | 5/2011 | Demarais et al. |
| 7,938,830 | B2 | 5/2011 | Saadat et al. |
| 7,942,874 | B2 | 5/2011 | Eder et al. |
| 7,942,928 | B2 | 5/2011 | Webler et al. |
| 7,946,976 | B2 | 5/2011 | Gertner |
| 7,950,397 | B2 | 5/2011 | Thapliyal et al. |
| 7,955,293 | B2 | 6/2011 | Nita et al. |
| 7,956,613 | B2 | 6/2011 | Wald |
| 7,959,627 | B2 | 6/2011 | Utley et al. |
| 7,962,854 | B2 | 6/2011 | Vance et al. |
| 7,967,782 | B2 | 6/2011 | Laufer et al. |
| 7,967,808 | B2 | 6/2011 | Fitzgerald et al. |
| 7,972,327 | B2 | 7/2011 | Eberl et al. |
| 7,972,330 | B2 | 7/2011 | Alejandro et al. |
| 7,983,751 | B2 | 7/2011 | Zdeblick et al. |
| 8,001,976 | B2 | 8/2011 | Gertner |
| 8,007,440 | B2 | 8/2011 | Magnin et al. |
| 8,012,147 | B2 | 9/2011 | Lafontaine |
| 8,019,435 | B2 | 9/2011 | Hastings et al. |
| 8,021,362 | B2 | 9/2011 | Deem et al. |
| 8,021,413 | B2 | 9/2011 | Dierking et al. |
| 8,025,661 | B2 | 9/2011 | Arnold et al. |
| 8,027,718 | B2 | 9/2011 | Spinner et al. |
| 8,031,927 | B2 | 10/2011 | Karl et al. |
| 8,033,284 | B2 | 10/2011 | Porter et al. |
| 8,048,144 | B2 | 11/2011 | Thistle et al. |
| 8,052,636 | B2 | 11/2011 | Moll et al. |
| 8,052,700 | B2 | 11/2011 | Dunn |
| 8,062,289 | B2 | 11/2011 | Babaev |
| 8,075,580 | B2 | 12/2011 | Makower |
| 8,080,006 | B2 | 12/2011 | Lafontaine et al. |
| 8,088,127 | B2 | 1/2012 | Mayse et al. |
| 8,116,883 | B2 | 2/2012 | Williams et al. |
| 8,119,183 | B2 | 2/2012 | O'Donoghue et al. |
| 8,120,518 | B2 | 2/2012 | Jang et al. |
| 8,123,741 | B2 | 2/2012 | Marrouche et al. |
| 8,128,617 | B2 | 3/2012 | Bencini et al. |
| 8,131,371 | B2 | 3/2012 | Demarals et al. |
| 8,131,372 | B2 | 3/2012 | Levin et al. |
| 8,131,382 | B2 | 3/2012 | Asada |
| 8,137,274 | B2 | 3/2012 | Weng et al. |
| 8,140,170 | B2 | 3/2012 | Rezai et al. |
| 8,143,316 | B2 | 3/2012 | Ueno |
| 8,145,316 | B2 | 3/2012 | Deem et al. |
| 8,145,317 | B2 | 3/2012 | Demarais et al. |
| 8,150,518 | B2 | 4/2012 | Levin et al. |
| 8,150,519 | B2 | 4/2012 | Demarais et al. |
| 8,150,520 | B2 | 4/2012 | Demarais et al. |
| 8,152,830 | B2 | 4/2012 | Gumm |
| 8,162,933 | B2 | 4/2012 | Francischelli et al. |
| 8,175,711 | B2 | 5/2012 | Demarais et al. |
| 8,187,261 | B2 | 5/2012 | Watson |
| 8,190,238 | B2 | 5/2012 | Moll et al. |
| 8,192,053 | B2 | 6/2012 | Owen et al. |
| 8,198,611 | B2 | 6/2012 | LaFontaine et al. |
| 8,214,056 | B2 | 7/2012 | Hoffer et al. |
| 8,221,407 | B2 | 7/2012 | Phan et al. |
| 8,226,637 | B2 | 7/2012 | Satake |
| 8,231,617 | B2 | 7/2012 | Satake |
| 8,241,217 | B2 | 8/2012 | Chiang et al. |
| 8,257,724 | B2 | 9/2012 | Cromack et al. |
| 8,257,725 | B2 | 9/2012 | Cromack et al. |
| 8,260,397 | B2 | 9/2012 | Ruff et al. |
| 8,263,104 | B2 | 9/2012 | Ho et al. |
| 8,273,023 | B2 | 9/2012 | Razavi |
| 8,277,379 | B2 | 10/2012 | Lau et al. |
| 8,287,524 | B2 | 10/2012 | Siegel |
| 8,287,532 | B2 | 10/2012 | Carroll et al. |
| 8,292,881 | B2 | 10/2012 | Brannan et al. |
| 8,293,703 | B2 | 10/2012 | Averback et al. |
| 8,295,902 | B2 | 10/2012 | Salahieh et al. |
| 8,295,912 | B2 | 10/2012 | Gertner |
| 8,308,722 | B2 | 11/2012 | Ormsby et al. |
| 8,317,776 | B2 | 11/2012 | Ferren et al. |
| 8,317,810 | B2 | 11/2012 | Stangenes et al. |
| 8,329,179 | B2 | 12/2012 | Ni et al. |
| 8,336,705 | B2 | 12/2012 | Okahisa |
| 8,343,031 | B2 | 1/2013 | Gertner |
| 8,343,145 | B2 | 1/2013 | Brannan |
| 8,347,891 | B2 | 1/2013 | Demarais et al. |
| 8,353,945 | B2 | 1/2013 | Andreas et al. |
| 8,364,237 | B2 | 1/2013 | Stone et al. |
| 8,366,615 | B2 | 2/2013 | Razavi |
| 8,382,697 | B2 | 2/2013 | Brenneman et al. |
| 8,388,680 | B2 | 3/2013 | Starksen et al. |
| 8,396,548 | B2 | 3/2013 | Perry et al. |
| 8,398,629 | B2 | 3/2013 | Thistle |
| 8,401,667 | B2 | 3/2013 | Gustus et al. |
| 8,403,881 | B2 | 3/2013 | Ferren et al. |
| 8,406,877 | B2 | 3/2013 | Smith et al. |
| 8,409,172 | B2 | 4/2013 | Moll et al. |
| 8,409,193 | B2 | 4/2013 | Young et al. |
| 8,409,195 | B2 | 4/2013 | Young |
| 8,418,362 | B2 | 4/2013 | Zerfas et al. |
| 8,452,988 | B2 | 5/2013 | Wang |
| 8,454,594 | B2 | 6/2013 | Demarais et al. |
| 8,460,358 | B2 | 6/2013 | Andreas et al. |
| 8,465,452 | B2 | 6/2013 | Kassab |
| 8,469,919 | B2 | 6/2013 | Ingle et al. |
| 8,473,067 | B2 | 6/2013 | Hastings et al. |
| 8,480,663 | B2 | 7/2013 | Ingle et al. |
| 8,485,992 | B2 | 7/2013 | Griffin et al. |
| 8,486,060 | B2 | 7/2013 | Kotmel et al. |
| 8,486,063 | B2 | 7/2013 | Werneth et al. |
| 8,488,591 | B2 | 7/2013 | Miali et al. |
| 2001/0007070 | A1 | 7/2001 | Stewart et al. |
| 2001/0039419 | A1 | 11/2001 | Francischelli et al. |
| 2002/0022864 | A1 | 2/2002 | Mahvi et al. |
| 2002/0042639 | A1 | 4/2002 | Murphy-Chutorian et al. |
| 2002/0045811 | A1 | 4/2002 | Kittrell et al. |
| 2002/0045890 | A1 | 4/2002 | Celliers et al. |
| 2002/0062146 | A1 | 5/2002 | Makower et al. |
| 2002/0065542 | A1 | 5/2002 | Lax et al. |
| 2002/0087151 | A1 | 7/2002 | Mody et al. |
| 2002/0095197 | A1 | 7/2002 | Lardo et al. |
| 2002/0107536 | A1 | 8/2002 | Hussein |
| 2002/0147480 | A1 | 10/2002 | Mamayek |
| 2002/0169444 | A1 | 11/2002 | Mest et al. |
| 2002/0198520 | A1 | 12/2002 | Coen et al. |
| 2003/0065317 | A1 | 4/2003 | Rudie et al. |
| 2003/0092995 | A1 | 5/2003 | Thompson |
| 2003/0139689 | A1 | 7/2003 | Shturman et al. |
| 2003/0195501 | A1 | 10/2003 | Sherman et al. |
| 2003/0199747 | A1 | 10/2003 | Michlitsch et al. |
| 2004/0010118 | A1 | 1/2004 | Zerhusen et al. |
| 2004/0019348 | A1 | 1/2004 | Stevens et al. |
| 2004/0024371 | A1 | 2/2004 | Plicchi et al. |
| 2004/0043030 | A1 | 3/2004 | Griffiths et al. |
| 2004/0064090 | A1 | 4/2004 | Keren et al. |
| 2004/0073206 | A1 | 4/2004 | Foley et al. |
| 2004/0088002 | A1 | 5/2004 | Boyle et al. |
| 2004/0093055 | A1 | 5/2004 | Bartorelli et al. |
| 2004/0106871 | A1 | 6/2004 | Hunyor et al. |
| 2004/0117032 | A1 | 6/2004 | Roth |

(56) References Cited

U.S. PATENT DOCUMENTS

| | | |
|---|---|---|
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0119647 A1 | 6/2005 | He et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004664 A1* | 1/2008 | Hopper et al. .............. 607/9 |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |

(56) References Cited

U.S. PATENT DOCUMENTS

| | | |
|---|---|---|
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0046618 A1 | 2/2011 | Minar et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |

(56) References Cited

U.S. PATENT DOCUMENTS

| | | |
|---|---|---|
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

"IntraLuminal: Products," IntraLuminal Therapeutics, Inc., 2003, p. 1-9.

"Laser Catheter to Aid Coronary Surgery," TechTalk: MIT, Jan. 9, 1991, p. 1-4.

"Optical Coherence Tomography: Advantages of OCT," LightLab Imaging Technology.

"Optical Coherence Tomography: Image Gallery Cardiovascular Procedures," LightLab Imaging Technology.

"Optical Coherence Tomography: LightLab Imaging Starts US Cardiology Clinical Investigations," LightLab Imaging Technology, 2002.

"Optical Coherence Tomography: LightLab Sees Bright Prospects for Cardiac Application of OCT Technology," LightLab Imaging Technology, 2001, vol. 27, No. 35.

"Optical Coherence Tomography: What is OCT?," LightLab Imaging Technology.

"Optical Coherence Tomography: Why Use OCT?," LightLab Imaging Technology.

(56) References Cited

OTHER PUBLICATIONS

"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.

Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Ciyoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.

(56) References Cited

OTHER PUBLICATIONS

Baun, "Interaction with Soft Tissue," Principles of General & Vascular Sonography, Chapter 2, pp. 23-24, Before Mar. 2012.

Blue Cross Blue Shield Medicaly Policy, "Surgery Section—MRI-Guided Focused Ultrasound (MRgFUS) for the Treatment of Uterine Fibroids and Other Tumors," 2005, 5 pages.

Gentry et al., "Combines 3D Intracardiac Echo and Ultrasound Ablation," Medical Imaging 2003: Ultrasonic and Signal Processing, vol. 5035, 2003, pp. 166-173.

Lafon et al., "Optmizing the Shape of Ultrasound Transducers for Interstitial Thermal Ablations," MEd Phys. Mar. 2002; 29(3): 290-7 (abstract only).

G. Ter Haar, "Ultrasound Focal Beam Surgery," Ultrasound in Med. & Biol., 1995, vol. 21, No. 9, pp. 1089-1100.

Seip et al., "Transurethral High Intensity Focused Ultrasound: Catheter Based Prototypes and Experimental Results," IEEE Ultrasonics Symposium Proceeding, 2000, 4 pages.

Toytman et al., "Tissue Dissection with Ultrafast Laser Using Extended and Multiple Foci," SPIE Proceeding, Optical Interactions with Tissues and Cells XXI, vol. 7562, 2010, 10 pages.

Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

US 8,398,630, 03/2013, Demarais et al. (withdrawn)

* cited by examiner

DEVICE AND METHODS FOR RENAL NERVE MODULATION MONITORING

CROSS-REFERENCE TO RELATED APPLICATIONS

This application claims priority under 35 U.S.C. §119 to U.S. Provisional Application Ser. No. 61/560,026, filed Nov. 15, 2011, the entirety of which is incorporated herein by reference.

TECHNICAL FIELD

The present invention relates to methods and apparatuses for nerve modulation techniques such as ablation of nerve tissue or other destructive modulation technique through the walls of blood vessels and monitoring thereof.

BACKGROUND

Certain treatments require the temporary or permanent interruption or modification of select nerve function. One example treatment is renal nerve ablation which is sometimes used to treat hypertension and other conditions related to hypertension and congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves (and nervous tissue such as brain tissue), including renal nerves, run along the walls of or in close proximity to blood vessels and thus can be accessed intravascularly through the walls of the blood vessels. In some instances, it may be desirable to ablate perivascular renal nerves using a radio frequency (RF) electrode in an off-wall configuration. However, the electrode and/or temperature sensors associated with the device may not be able to detect tissue changes in the target region because the electrode is not in contact with the wall. Sensing electrodes may allow the use of impedance measuring to monitor tissue changes. It is therefore desirable to provide for alternative systems and methods for intravascular nerve modulation.

SUMMARY

The disclosure is directed to several alternative designs, materials and methods of manufacturing medical device structures and assemblies for performing and monitoring tissue changes.

Accordingly, one illustrative embodiment is a system for nerve modulation that may include an elongate shaft having a proximal end region and a distal end region. An ablation electrode and a first sensing electrode may be disposed on the elongate shaft adjacent to distal end region. The system may further include a ground pad. The ablation electrode, sensing electrode, and ground pad may be electrically connected to a control unit.

Another illustrative embodiment is a method for detecting tissue changes during tissue modulation. A tissue modulation system including an elongate shaft having a proximal end region and a distal end region may be provided. The modulation system may further include a first electrode disposed adjacent the distal end region and a second electrode disposed adjacent to the distal end region and spaced a distance from the first electrode. The modulation system may be advanced through a lumen such that the distal end region is adjacent to a target region. Voltage may be applied to the modulation system to impart a current between the first and second electrodes and an impedance of the target region may be calculated from the current. Voltage may be applied to at least one of the first or second electrodes to effect tissue modulation on the target region. The current between the first and second electrodes may be monitored for changes in the impedance of the target region.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
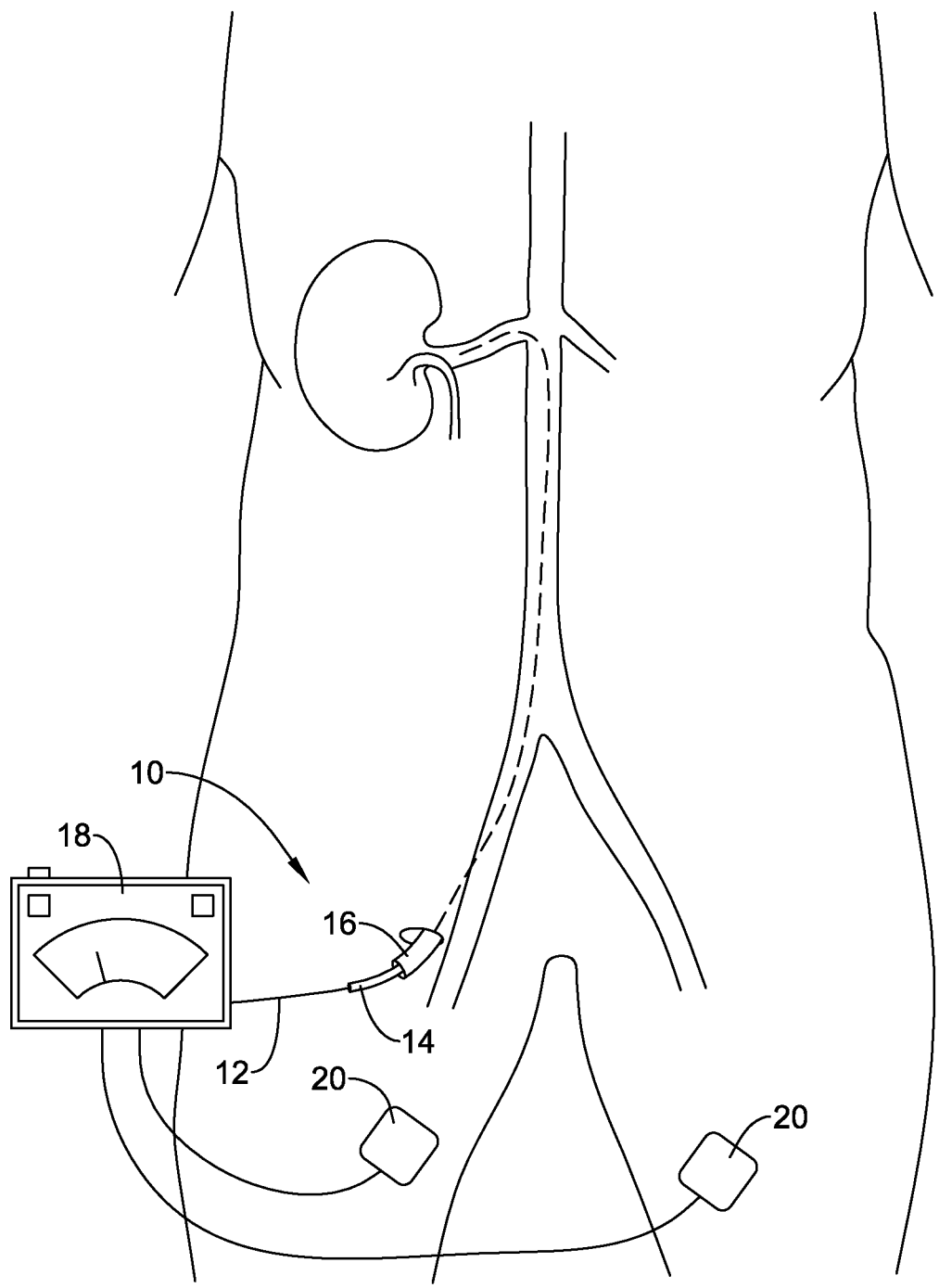
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

While the devices and methods described herein are discussed relative to renal nerve modulation, it is contemplated that the devices and methods may be used in other applications where nerve modulation and/or ablation are desired. For example, the devices and methods described herein may also be used for prostate ablation, tumor ablation, and/or other therapies requiring heating or ablation of target tissue. In some instances, it may be desirable to ablate perivascular renal nerves with deep target tissue heating. As energy passes from a modulation element to the desired treatment region the energy may heat both the tissue and the intervening fluid (e.g. blood) as it passes. As more energy is used, higher temperatures in the desired treatment region may be achieved thus resulting in a deeper lesion. Monitoring tissue properties may, for example, verify effective ablation, improve safety, and optimize treatment time.

In some instances, ablation is performed with the modulation element in direct contact with the vessel or chamber wall. The modulation element may contain a thermistor or thermocouple which facilitates monitoring of the ablation progress by providing a real-time temperature signal. However, in some instances, it may be advantageous to move the modulation element away from the vessel wall in an off-the-wall configuration, such as when circumferential ablation is desired. During circumferential ablation, the modulation element may be positioned at the center of the lumen. However, when the modulation element does not contact the vessel wall it may be difficult to detect tissue changes during and/or after the ablation process. When provided in an off-the-wall configuration, the modulation element, and thus any temperature sensing means provided on or adjacent to the ablation electrode, may be cooled by the blood flow surrounding the modulation element. As such, thermal feedback may not be useful to provide monitoring as the ablation is performed, resulting in a "blind" ablation scenario. Although the ability to monitor the tissue properties during circumferential ablation may be reduced or require additional sensing elements, off-the-wall ablation may allow for free flow of blood across the vessel surface minimizing heat damage to the vessel wall due to the ablation process.

In some instances, impedance monitoring may be used to detect changes in target tissues as ablation progresses. Sensing electrodes may be provided in addition to the modulation element. In some instances, the impedance may not be directly measured, but may be a function of the current distribution between the sensing electrodes. In general, the resistance of the surrounding tissue may decrease as the temperature of the tissue increases until a point where the tissue begins to denature or irreversibly change, for example, at approximately 50-60° C. Once the tissue has begun to denature the resistance of the tissue may increase. As the target tissue is ablated, the change in impedance may be analyzed to determine how much tissue has been ablated. The power level and duration of the ablation may be adjusted accordingly based on the impedance of the tissue.

FIG. 1 is a schematic view of an illustrative renal nerve modulation system 10 in situ. System 10 may include an element 12 for providing power to a nerve modulation element disposed about and/or within a central elongate shaft 14 and, optionally, within a sheath or guide catheter 16. A proximal end of element 12 may be connected to a control and power element 18, which supplies the necessary electrical energy to activate the one or more modulation elements at or near a distal end of the element 12. In some instances, return electrode patches 20 may be supplied on the legs or at another conventional location on the patient's body to complete the circuit. The control and power element 18 may include monitoring elements to monitor parameters such as power, temperature, voltage, pulse size, and/or shape and other suitable parameters as well as suitable controls for performing the desired procedure. In some instances, the power element 18 may control a radio frequency (RF) ablation electrode and/or one or more sensing electrodes. It is contemplated that more than one power element 18 may be provided. In some instances, the ablation electrode and the sensing electrode may be connected to separate power elements 18. The ablation electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser to perform the ablation. While the term ablation electrode is used herein, it is contemplated that the modulation element and modulation frequency may be selected according to the energy used to perform the ablation. For example, when ultrasound energy is used, an ultrasonic transducer may be selected as the modulation element and modulation frequencies may be in the MHz range. The sensing electrodes may be configured to operate over frequency ranges which are different from the frequency range at which the ablation is being performed. It is contemplated that the sensing electrodes may be operated over a range of frequencies for improved impedance measuring.

Figure 2:
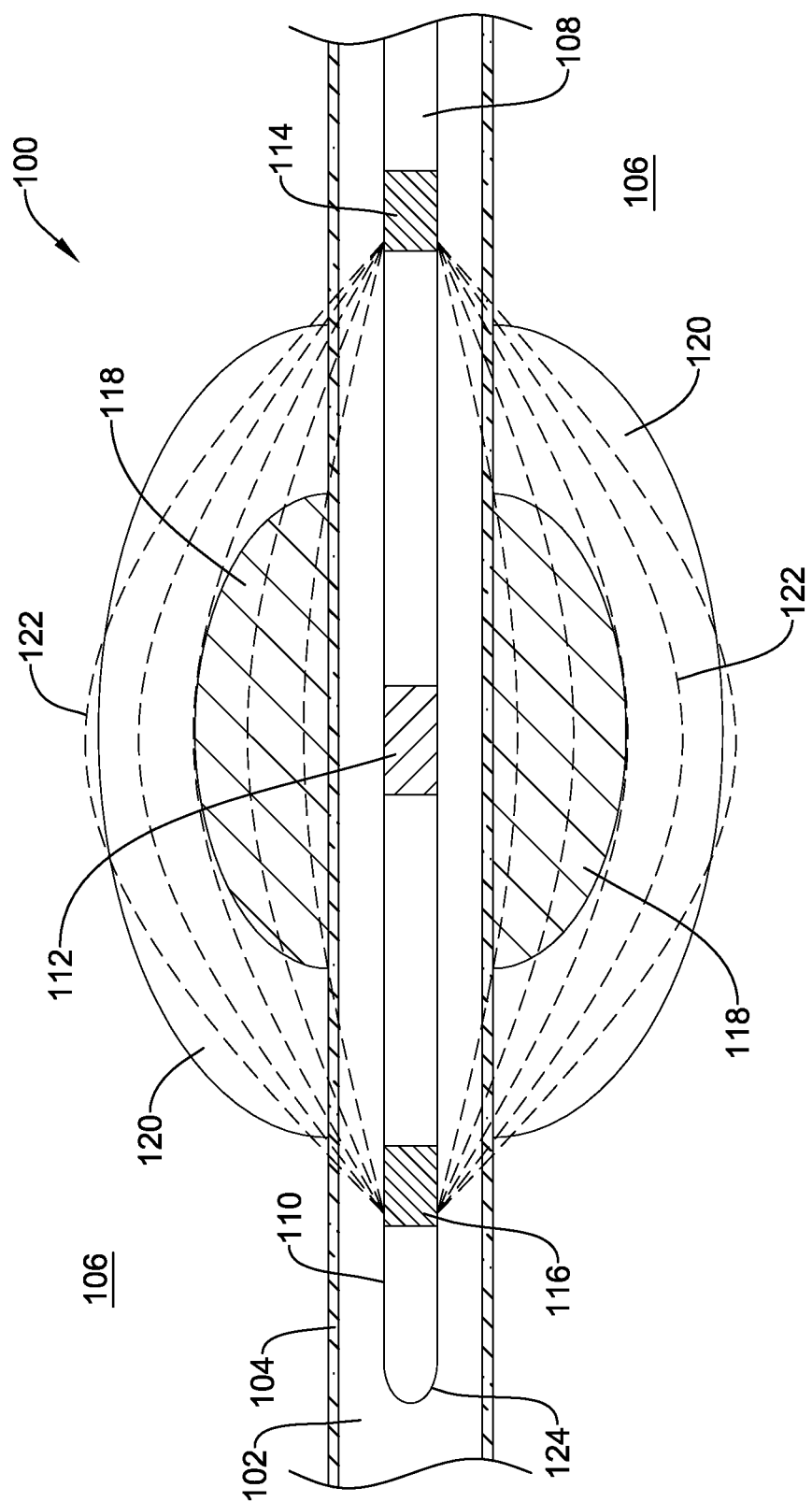
FIG. 2 illustrates a distal end of an illustrative renal nerve modulation system.

FIG. 2 is an illustrative embodiment of a distal end of a renal nerve modulation system 100 disposed within a body lumen 102 having a vessel wall 104. The vessel wall 104 may be surrounded by additional body tissue 106. A portion of the tissue 106 may be the desired treatment region 118, 120, as will be discussed in more detail below. The system 100 may include an elongate shaft 108 having a distal end region 110. The elongate shaft 108 may extend proximally from the distal end region 110 to a proximal end configured to remain outside of a patient's body. The proximal end of the elongate shaft 108 may include a hub attached thereto for connecting other treatment devices or providing a port for facilitating other treatments. It is contemplated that the stiffness of the elongate shaft 108 may be modified to form a modulation system 100 for use in various vessel diameters and various locations within the vascular tree. The elongate shaft 108 may further include one or more lumens extending therethrough. For example, the elongate shaft 108 may include a guidewire lumen and/or one or more auxiliary lumens. The lumens may be configured in any way known in the art. For example, the guidewire lumen may extend the entire length of the elongate shaft 108 such as in an over-the-wire catheter or may extend only along a distal portion of the elongate shaft 108 such as in a single operator exchange (SOE) catheter. These examples are not intended to be limiting, but rather examples of some possible configurations. While not explicitly shown, the modulation system 100 may further include temperature sensors/wire, an infusion lumen, radiopaque marker bands, fixed guidewire tip, a guidewire lumen, external sheath and/or other components to facilitate the use and advancement of the system 100 within the vasculature.

The system 100 may further include one or more ablation electrodes 112 disposed on the outer surface of the elongate shaft 108 adjacent the distal end region 110. However, the ablation electrode 112 may be placed at any longitudinal location along the elongate shaft desired. While the system 100 is illustrated as including one ablation electrode 112, it is contemplated that the modulation system 100 may include any number of ablation electrodes 112 desired, such as, but not limited to, two, three, four, or more. If multiple ablation electrodes 112 are provided, the ablation electrodes 112 may be longitudinally, radially and/or circumferentially spaced as desired. In some instances, the ablation electrode 112 may be a circumferential electrode extending around the outer perimeter of the elongate shaft 108. A circumferential electrode 112 may allow for circumferential ablation while reducing and/or eliminating the need for circumferential repositioning of the electrode 112 and/or elongate shaft 108. In some embodiments, the ablation electrode 112 may not extend all the way around the perimeter of the elongate shaft 108. It is contemplated that multiple ablation electrodes 112 may be circumferentially positioned around the perimeter of the elongate shaft 108 to reduce and/or eliminate the need to circumferentially reposition the elongate shaft 108 to perform 360° ablation.

In some embodiments, the ablation electrode 112 may be formed of a separate structure and attached to the elongate shaft 108. For example, the ablation electrode 112 may be machined or stamped from a monolithic piece of material and subsequently bonded or otherwise attached to the elongate shaft 108. In other embodiments, the ablation electrode 112 may be formed directly on the surface of the elongate shaft 108. For example, the ablation electrode 112 may be plated, printed, or otherwise deposited on the surface. In some instances, the ablation electrode 112 may sufficiently radiopaque so that it also functions as a radiopaque marker. The ablation electrode 112 may be formed from any suitable material such as, but not limited to, platinum, gold, stainless steel, cobalt alloys, or other non-oxidizing materials. In some instances, titanium, tantalum, or tungsten may be used. It is contemplated that the ablation electrode 112 may take any shape desired, such as, but not limited to, square, rectangular, circular, elliptical, etc. In some embodiments, the ablation electrode 112 may have rounded edges in order to reduce the affects of sharp edges on current density. The size of the ablation electrode 112 may be chosen to optimize the current density without increasing the profile of the modulation system 100. For example, an ablation electrode 112 that is too small may generate high local current densities resulting in greater heat transfer to the blood and surrounding tissues. An ablation electrode 112 that is too large may require a larger elongate shaft 108 to carry it. In some instances, the ablation electrode 112 may have an aspect ratio of 2:1 (length to width) or greater. Such an elongated structure may provide the ablation electrode 112 with more surface area without increasing the profile of the modulation system 100.

During the ablation procedure, the ablation electrode 112 may be positioned away from the vessel wall 104 in an off-the-wall configuration. While not explicitly shown, modulation system 100 may further include structure to maintain the ablation electrode 112 in the off-the-wall configuration. For example, in some instances, the elongate shaft may further include a positioning basket configured to expand and engage the vessel wall 104 to center the electrode 112. In other embodiments, elongate shaft 108 may further include a partially occlusive balloon which may be used to position the ablation electrode 112 and/or to increase the blood velocity near the ablation electrode 112 to provide better vessel wall 104 cooling. It is further contemplated that the ablation electrode 112 and/or sensing electrodes 114, 116 may be positioned on a positioning basket and/or balloon.

The modulation system 100 may further include a proximal sensing electrode 114 and a distal sensing electrode 116. The proximal sensing electrode 114 may be located proximal of the ablation electrode 112 and the distal sensing electrode 116 may be located distal of the ablation electrode 112. In some embodiments, the distal sensing electrode 116 may be located proximal of the distal end 124 of the elongate shaft 108. In other embodiments, the distal sensing electrode 116 may be adjacent to the distal end 124 of the elongate shaft 108. While the system is illustrated as including two sensing electrodes 114, 116, it is contemplated that fewer than or more than two sensing electrodes 114, 116 may be provided to improve or provide additional impedance information. In some embodiments, the sensing electrodes may be high-impedance sensing electrodes. This may minimize the field distortion during the measurement. However, in some instances, low-impedance sensing electrodes may be used.

The sensing electrodes 114, 116 may be used to monitor the impedance of the tissue separating them. Impedance sensing current 122 may pass between the proximal 114 and distal 116 sensing electrodes. For clarity, not all of the potential current paths 122 have been illustrated or numbered. For example, it is contemplated that some current may pass through the bloodstream between the sensing electrodes 114, 116. As ablation of the target region 118, 120 progresses, the impedance properties of the surrounding tissue 118, 120 may change thus changing the impedance calculated between the proximal sensing electrode 114 and the distal sensing electrode 116. The sensing electrodes 114, 116 may be symmetrically placed about the ablation electrode 112 such that they can easily track the change which occurs to the tissue impedance in the ablation zone 118, 120 located between them. This may provide improved signal-to-noise ratio for better real-time monitoring of the ablation progress. However, the sensing electrodes 114, 116 may be arranged in any orientation desired and need not be symmetrical about the ablation electrode 112. While the sensing electrodes 114, 116 are illustrated in a non-contact ablation system 100 it is contemplated that the sensing electrodes 114, 116 may be used in systems where the ablation electrode 112 contacts the vessel wall 104.

In some embodiments, the sensing electrodes 114, 116 may be formed of a separate structure and attached to the elongate shaft 108. For example, the sensing electrodes 114, 116 may be machined or stamped from a monolithic piece of material and subsequently bonded or otherwise attached to the elongate shaft 108. In other embodiments, sensing electrodes 114, 116 may be formed directly on the surface of the elongate shaft 108. For example, the sensing electrodes 114, 116 may be plated, printed, or otherwise deposited on the surface. In some instances, the sensing electrodes 114, 116 may also function as radiopaque marker bands. The sensing electrodes 114, 116 may be formed from any suitable material such as, but not limited to, platinum, gold, stainless steel, cobalt alloys, or other non-oxidizing materials. In some instances, titanium, tantalum, or tungsten may be used. It is contemplated that the sensing electrodes 114, 116 may take any shape desired, such as, but not limited to, square, rectangular, circular, oblong, etc. The size of the sensing electrodes 114, 116 may be chosen to optimize the current density without increasing the profile of the modulation system 100.

While not explicitly shown, the sensing electrodes 114, 116 may be connected to the control unit (such as control unit 18 in FIG. 1) by electrical conductors. In some embodiments the sensing electrodes 114, 116 may be on a separate electrical circuit from the ablation electrode 112 and from each other. The sensing electrodes 114, 116 may be operated at a different frequency than the ablation electrode 112. For example, the frequency, duty cycle, and shape of the excitation waveform of the sensing electrodes 114, 116 can be adapted to yield an optimized signal-to-noise ratio for each of the tissue parameters monitored. In some instances, the sensing electrodes 114, 116 may be operated simultaneously with the ablation electrode 112 to provide real-time feedback of the ablation progress. In other embodiments, the sensing electrodes 114, 116 may be operated in an alternating fashion (e.g. an ablation/sensing duty cycle) with the ablation electrode 112 such that the sensing electrodes 114, 116 and the ablation electrode 112 are not simultaneously active.

While not explicitly shown, the ablation electrode 112 may be connected to a control unit (such as control unit 18 in FIG. 1) by electrical conductors. Once the modulation system 100 has been advanced to the treatment region, energy may be supplied to the ablation electrode 112. The amount of energy delivered to the ablation electrode 112 may be determined by the desired treatment as well as the feedback obtained from the sensing electrodes 114, 116. As discussed above, once the target tissue 118, 120 has begun to denature the resistance of the tissue may increase. The target region 118 nearest the ablation electrode 112 may receive more energy than the target region 120 positioned further away from the ablation electrode 112 and thus may begin to denature more quickly. As the target tissue 118, 120 is ablated, the change in impedance in the tissue 118, 120 may be analyzed to determine how much tissue has been ablated and/or the degree of denaturing. The power level and duration of the ablation may be adjusted accordingly based on the impedance of the tissue. For example, more energy may result in a larger, deeper lesion.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 16 shown in FIG. 1. Once the ablation electrode 112 of the modulation system 100 has been placed adjacent to the desired treatment area, positioning mechanisms may be deployed, if so provided. While not explicitly shown, the ablation electrode 112 and the sensing electrodes 114, 116 may be connected to a single control unit or to separate control units (such as control unit 18 in FIG. 1) by electrical conductors. Once the modulation system 100 has been advanced to the treatment region, energy may be supplied to the ablation electrode 112 and the sensing electrodes 114, 116. As discussed above, the energy may be supplied to both the ablation electrode 112 and sensing electrodes 114, 116 simultaneously or in an alternating fashion at desired. The amount of energy delivered to the ablation electrode 112 may be determined by the desired treatment as well as the feedback provided by the sensing electrodes 114, 116.

It is contemplated if an ablation electrode 112 is provided that does not extend around the entire circumference of the elongate shaft 108, the elongate shaft 108 may need to be circumferentially repositioned and energy may once again be delivered to the ablation electrode 112 and the sensing electrodes 114, 116 to adequately ablate the target tissue. The number of times the elongate shaft 108 is rotated at a given longitudinal location may be determined by the number and size of the ablation electrode(s) 112 on the elongate shaft 108. Once a particular location has been ablated, it may be desirable to perform further ablation procedures at different longitudinal locations. Once the elongate shaft 108 has been longitudinally repositioned, energy may once again be delivered to the ablation electrode 112, and the sensing electrodes 114, 116. If necessary, the elongate shaft 108 may be circumferentially repositioned at each longitudinal location. This process may be repeated at any number of longitudinal locations desired. It is contemplated that in some embodiments, the system 100 may include ablation electrodes 112 at various positions along the length of the modulation system 100 such that a larger region may be treated without longitudinal displacement of the elongate shaft 108.

While FIG. 2 illustrates the sensing electrodes 114, 116 in an off-the-wall configuration, is contemplated that one or both of the sensing electrodes 114, 116 may be placed in direct contact with the vessel wall 104. As the sensing electrodes 114, 116 may be operated at a frequency and amplitude which does not result in tissue ablation, placing the sensing electrodes 114, 116 against the vessel wall 104 will not cause the vessel damage. In instances where direct contact ablation is acceptable, the ablation electrode 112 may also be placed in contact with the vessel wall 104. It is contemplated that the elongate shaft 108 may further include an infusion lumen configured to perfuse the vessel lumen 102 with saline or other conductive fluid during the ablation procedure. In some instances, the perfused fluid may be provided at room temperature or cooler.

Figure 3:
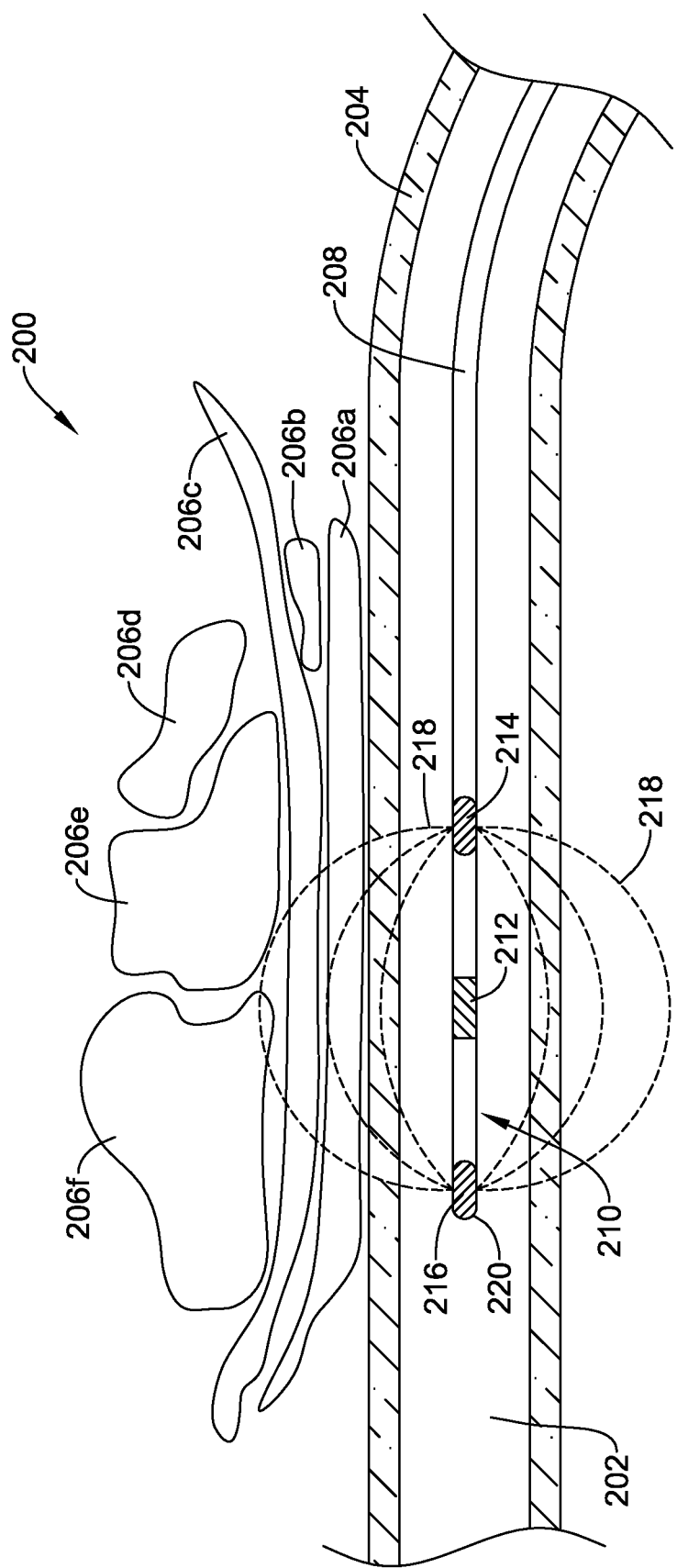
FIG. 3 illustrates a distal end of another illustrative renal nerve modulation system.

FIG. 3 is an illustrative embodiment of a distal end of a renal nerve modulation system 200 that may be similar in form and function to other systems disclosed herein. The modulation system may be disposed within a body lumen 202 having a vessel wall 204. The vessel wall 204 may be surrounded by additional body tissues 206a-f. There may be several different tissue types 206a-f surrounding the vessel wall 204. For example, the tissues 206a-f may comprise adventitia and connective tissues, nerves, fat, fluid, etc. in addition to the muscular vessel wall 204. It is contemplated that some of the body tissues 206a-f may be the same type of tissue or may be all different types of tissue. The body tissues 206a-f shown in FIG. 3 is not intended to fully represent the tissue composition surrounding a vessel wall 204, but rather illustrate that different tissue types and sizes may surround the vessel wall 204. It is to be further understood that while FIG. 3 illustrated the body tissues 206a-f on a single side of the vessel wall, the body tissues 206a-f may surround the perimeter of the vessel wall 204 and is not limited to one side.

Each of the different types of tissue 206a-f may have different electrical properties (e.g. impedance, permittivity, conductivity, etc.) and may also have different changes in those properties due to thermal ablation. Variation in local tissue types 206a-f and impedance may cause unpredictable variation in the ablation effect on the target tissue and in local artery wall heating. It may be desirable to characterize local tissues and monitor tissue changes in order to control the energy delivery for proper target tissue ablation. The nerve modulation system 200 may include two or more sensing electrodes 214, 216 to determine one or more impedance values over a range of frequencies. It is contemplated that tissue impedance may be monitored during RF, ultrasound, laser, microwave, or other ablation. The frequency at which the sensing electrodes 214, 216 are operated may be chosen according to the tissue material present or expected to be present. The impedance may be used to evaluate which type(s) of tissue are adjacent to the ablation region and to monitor changes which occur by thermal ablation of that tissue(s).

The system 200 may include an elongate shaft 208 having a distal end region 210 and a distal end 220. The elongate shaft 208 may extend proximally from the distal end 220 to a proximal end configured to remain outside of a patient's body. The proximal end of the elongate shaft 208 may include a hub attached thereto for connecting other treatment devices or providing a port for facilitating other treatments. It is contemplated that the stiffness of the elongate shaft 208 may be modified to form modulation system 200 for use in various vessel diameters. The elongate shaft 208 may further include one or more lumens extending therethrough. For example, the elongate shaft 208 may include a guide wire lumen and/or one or more auxiliary lumens. The lumens may be configured in any suitable way such as those ways commonly used for medical devices. While not explicitly shown, the modulation system 200 may further include temperature sensors/wire, an infusion lumen, radiopaque marker bands, fixed guidewire tip, external sheath and/or other components to facilitate the use and advancement of the system 200 within the vasculature.

The system 200 may further include one or more ablation electrodes 212 disposed on the outer surface of the elongate shaft 208. While the system 200 is illustrated as including a single ablation electrode 212, it is contemplated that the modulation system 200 may include any number of ablation electrodes 212 desired, such as, but not limited to, two, three, four, or more. If multiple ablation electrodes 212 are provided, the ablation electrodes 212 may be longitudinally and/or radially spaced as desired. The ablation electrode 212 may include similar features and may function in a similar manner to the ablation electrode discussed with respect to FIG. 2.

During the ablation procedure, the ablation electrode 212 may be positioned away from the vessel wall 204 in an off-the-wall configuration. While not explicitly shown, the modulation system 200 may further include structure to maintain the ablation electrode 212 in the off-the-wall configuration. For example, in some instances the elongate shaft may further include a positioning basket configured to expand and engage the vessel wall 204 to center the electrode 212. In other embodiments elongate shaft 208 may further include a partially occlusive balloon which may be used to position the ablation electrode 212 and/or to increase the blood velocity near the ablation electrode 212 to provide better vessel wall cooling. It is further contemplated that the ablation electrode 212 and/or sensing electrodes 214, 216 may be positioned on a positioning basket and/or balloon.

The modulation system 200 may further include a proximal sensing electrode 214 and a distal sensing electrode 216. It is contemplated that the modulation system 200 may include more than two sensing electrodes 214, 216 to further refine the tissue evaluation. The sensing electrodes 214, 216 may include similar features and may function in a similar manner to the sensing electrodes discussed with respect to FIG. 2. In some instances, high impedance sensing electrodes 214, 216 may be used in order to avoid significant distortion of the electric field and to avoid bipolar ablation between the ablation electrode 212 and the sensing electrodes 214, 216. The proximal sensing electrode 214 may be located proximal of the ablation electrode 212 and the distal sensing electrode 216 may be located distal of the ablation electrode 212. In some embodiments, the distal sensing electrode 216 may be located adjacent to the distal end 220 of the elongate shaft 208. In other embodiments, the distal sensing electrode 216 may be proximal of the distal end 220 of the elongate shaft 208.

The sensing electrodes 214, 216 may be used to monitor the impedance of the tissue separating them. While not explicitly shown, the sensing electrodes 214, 216 may be connected through separate insulated conductors to a control unit (such as control unit 18 illustrated in FIG. 1). In some embodiments the sensing electrodes 214, 216 may be on a separate electrical circuit from the ablation electrode 212. The sensing electrodes 214, 216 may be operated at a different frequency than the ablation electrode 212. For example, the frequency, duty cycle, and shape of the excitation waveform of the sensing electrodes 214, 216 can be adapted to yield an optimized signal-to-noise ratio for each of the tissue parameters monitored. When voltage is applied across the sensing electrodes 214, 216, a small current 218 may flow through the tissues 206*a-f*. For clarity, not all of the potential current paths 218 have been illustrated or numbered. For example, it is contemplated that some current may pass through the bloodstream in lumen 202. The current 218 may be monitored by the control unit and used to determine the local tissue impedance in the vicinity of the sensing electrodes 214, 216. Various frequencies may be used to determine one or more impedance values, or a simpler calculation of resistance at low frequently can be utilized. Tissue impedance may vary at different temperatures and may also be affected by protein changes, perfusion changes, and fluid changes as a result of thermal ablation. The different tissues have different electrical properties and also react differently to thermal ablation. The impedance measurements may be used to determine which tissues are in the local ablation region, and to monitor changes which occur by ablation of those tissues. The use of various frequencies may allow for better discrimination between tissue types and monitoring of ablative changes. Accordingly, ongoing impedance monitoring may be used to evaluate whether the modulation system 200 and positioned appropriately treat target tissue and determine when ablation has been completed. It is contemplated that undesired changes, such as ablative changes to the muscular vessel wall 204, can also be detected.

Tissue impedance may be monitored during simultaneous RF ablation (e.g. energy is applied simultaneously to the ablation electrode 212 and the sensing electrodes 214, 216). In such a case, most of the current may flow between the ablation electrode 212 and a skin contact ground pad (such as ground contact pad 20 in FIG. 1) and through the perivascular target tissues to be ablated, while a small amount of current may flow between the ablation electrode 212 and at least one higher impedance sensing electrode 214, 216. In this instance, it is contemplated that body impedance between the ablation electrode 212 and skin contact ground pad may also be measured. It is further contemplated that tissue impedance may be monitored during ablation/sensing duty cycle which may be used alternate between ablation and impedance measurement. As ablation of the target region progresses, the impedance properties of the surrounding tissues 206*a-f* may change thus changing the impedance calculated between the proximal sensing electrode 214 and the distal sensing electrode 216, between the ablation electrode 212 and the contact ground pad, and/or between the ablation electrode 212 and one or more sensing electrodes 214, 216.

While not explicitly shown, the ablation electrode 212 may be connected to a control unit (such as control unit 18 in FIG. 1) by electrical conductors. Once the modulation system 200 has been advanced to the treatment region, energy may be supplied to the ablation electrode 212. The amount of energy delivered to the ablation electrode 212 may be determined by the desired treatment as well as the feedback obtained from the sensing electrodes 214, 216. As discussed above, once the target tissue has begun to denature the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 200 may monitor impedance values of the surrounding tissues 206a-f prior to beginning the ablation procedure and adjust the ablation parameters accordingly. It is further contemplated that other electrical properties of the tissues 206a-f such as permittivity and/or conductivity may be used to set the current and/or power for RF or other ablation energy to target tissues.

The modulation system 200 may be advanced through the vasculature in any manner known in the art. For example, system 200 may include a guidewire lumen to allow the system 200 to be advanced over a previously located guidewire. In some embodiments, the modulation system 200 may be advanced, or partially advanced, within a guide sheath such as the sheath 16 shown in FIG. 1. Once the ablation electrode 212 of the modulation system 200 has been placed adjacent to the desired treatment area, positioning mechanisms may be deployed, if so provided. While not explicitly shown, the ablation electrode 212 and the sensing electrodes 214, 216 may be connected to a single control unit or to separate control units (such as control unit 18 in FIG. 1) by electrical conductors. Once the modulation system 200 has been advanced to the treatment region, energy may be supplied to the ablation electrode 212 and the sensing electrodes 214, 216. As discussed above, the energy may be supplied to both the ablation electrode 212 in sensing electrodes 214, 216 simultaneously or in an alternating duty cycle at desired. The amount of energy delivered to the ablation electrode 212 may be determined by the desired treatment as well as the feedback provided by the sensing electrodes 214, 216.

It is contemplated if an ablation electrode 212 is provided that does not extend around the entire circumference of the elongate shaft 208, the elongate shaft 208 may need to be circumferentially repositioned and energy may once again be delivered to the ablation electrode 212 and the sensing electrodes 214, 216 to adequately ablate the target tissue ablation. The number of times the elongate shaft 208 is rotated at a given longitudinal location may be determined by the number and size of the ablation electrode(s) 212 on the elongate shaft 208. Once a particular location has been ablated, it may be desirable to perform further ablation at different longitudinal locations. Once the elongate shaft 208 has been longitudinally repositioned, energy may once again be delivered to the ablation electrode 212, and the sensing electrodes 214, 216. If necessary, the elongate shaft 208 may be circumferentially repositioned at each longitudinal location. This process may be repeated at any number of longitudinal locations desired. It is contemplated that in some embodiments, the system 200 may include ablation electrodes 212 at various positions along the length of the modulation system 200 such that a larger region may be treated without longitudinal displacement of the elongate shaft 208.

While FIG. 3 illustrates the sensing electrodes 214, 216 in an off-the-wall configuration, it is contemplated that one or both of the sensing electrodes 214, 216 may be placed in direct contact with the vessel wall 204. As the sensing electrodes 214, 216 may be operated at a frequency and amplitude which does not result in tissue ablation, placing the sensing electrodes 214, 216 against the vessel wall 204 will not cause the vessel damage. In instances where direct contact ablation is acceptable, the ablation electrode 212 may also be placed in contact with the vessel wall 204. It is contemplated that the elongate shaft 208 may further include an infusion lumen configured to perfuse the vessel lumen 202 with saline or other conductive fluid during the ablation procedure. In some instances, the perfused fluid may be provided at room temperature or cooler.

Figure 4:
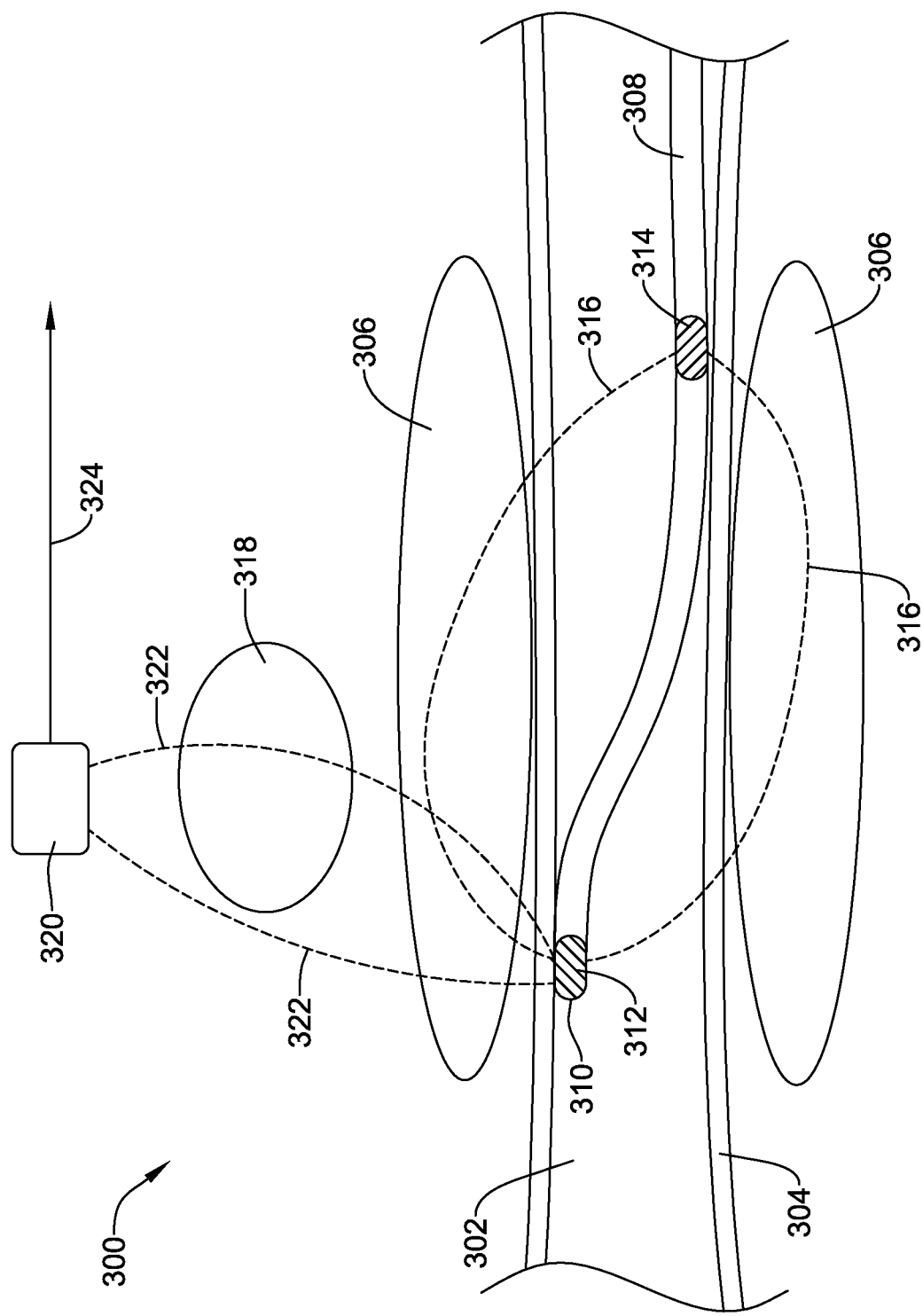
FIG. 4 illustrates a distal end of another illustrative renal nerve modulation system.

FIG. 4 is an illustrative embodiment of a distal end of a renal nerve modulation system 300 that may be similar in form and function to other systems disclosed herein. The modulation system 300 may be disposed within a body lumen 302 having a vessel wall 304. The vessel wall 304 may be surrounded by local target tissue 306. It may be desirable to determine local tissue impedance and monitor tissue changes in order to control the energy delivery for proper target tissue ablation. The nerve modulation system 300 may include a high-impedance sensing electrode 314 to determine local impedance. It is contemplated that tissue impedance may be monitored during RF, ultrasound, laser, microwave, or other ablation methods.

The system 300 may include an elongate shaft 308 having a distal end 310. The elongate shaft 308 may extend proximally from the distal end 310 to a proximal end configured to remain outside of a patient's body. The proximal end of the elongate shaft 308 may include a hub attached thereto for connecting other treatment devices or providing a port for facilitating other treatments. It is contemplated that the stiffness of the elongate shaft 308 may be modified to form modulation system 300 for use in various vessel diameters. The elongate shaft 308 may further include one or more lumens extending therethrough. For example, the elongate shaft 308 may include a guide wire lumen and/or one or more auxiliary lumens. The lumens may be configured in any suitable way such as those ways commonly used for medical devices. While not explicitly shown, the modulation system 300 may further include temperature sensors/wires, an infusion lumen, radiopaque marker bands, fixed guidewire tip, external sheath and/or other components to facilitate the use and advancement of the system 300 within the vasculature.

The system 300 may further include one or more ablation electrodes 312 disposed on the outer surface of the elongate shaft 308. While the system 300 is illustrated as including one ablation electrode 312, it is contemplated that the modulation system 300 may include any number of ablation electrodes 312 desired, such as, but not limited to, two, three, four, or more. If multiple ablation electrodes 312 are provided, the ablation electrodes 312 may be longitudinally and/or radially and/or circumferentially spaced as desired. The ablation electrode 312 may include similar features and may function in a similar manner to the ablation electrode discussed with respect to FIG. 2. In some embodiments, the ablation electrode 312 may be positioned adjacent to the distal end 310 of the elongate shaft 308. In other embodiments, the ablation electrode 312 may be positioned proximal of the distal end 310.

The modulation system 300 may further include a sensing electrode 314. It is contemplated that the modulation system 300 may include more than one sensing electrode 314 to further refine the tissue evaluation. The sensing electrode 314 may include similar features and may function in a similar manner to the sensing electrode discussed with respect FIG. 2. In some instances, a high impedance sensing electrode 314 may be used in order to avoid significant distortion of the electric field and to avoid bipolar ablation between the ablation electrode 312 and the sensing electrode 314. In some embodiments, the sensing electrode 314 may be located proximal of the ablation electrode 312. In other embodiments, the sensing electrode 314 may be located distal of the ablation electrode 312.

The ablation electrode 312 and the sensing electrode 314 may be used to monitor the impedance of the local tissue 306.

While not explicitly shown, the ablation electrode 312 and the sensing electrode 314 may be connected through separate insulated conductors to a control unit (such as control unit 18 in FIG. 1). A skin-contact ground pad 320 may also be connected through an electrical conductor 324 to the control unit. As voltage is applied to the ablation electrode 312, current 322 may pass through the local tissue 306 and additional body tissue 318 to the ground pad 320. During ablation, the sensing electrode 314 may be used as a reference electrode and measure the local voltage at a known location in the local tissue 306, which may be monitored by the control unit. The local voltage may be used to determine the local tissue impedance between the ablation electrode 312 and the sensing electrode 314. Various frequencies may be used to determine one or more impedance values, or a simpler calculation of resistance at low frequency can be utilized.

Tissue impedance may be monitored during simultaneous RF ablation (e.g. energy is applied simultaneously to the ablation electrode 312 and the sensing electrodes 314). In such a case, most of the current 322 may flow between the ablation electrode 312 and the skin-contact ground pad 320 and through the perivascular target tissues to be ablated, while a small amount of current 316 may flow between the ablation electrode 312 and the high impedance sensing electrode 314. In this instance, the body impedance resulting from body tissue 318 outside of the target tissue region 306 between the ablation electrode 312 and skin contact ground pad 320 may also be measured. Tissue distribution and make-up may vary from patient to patient. For example, in some instances, a large portion of the power applied to the system 300 (e.g. approximately 80% in some cases) may be distributed locally, or within approximately two to three radii of the ablation electrode 312, while the remaining portion (e.g. approximately 20%) is distributed throughout the remainder of the body (e.g across the skin, subcutaneous fat, and/or other tissue not in the local target tissue 306). As the body composition may vary from person to person, the power distribution may also vary. The modulation system 300 may be configured to normalize the voltage supplied to the ablation electrode 312 to account for variations in impedance of the patient's body. It is contemplated that the local voltage (e.g. the difference between the voltage at the ablation electrode 312 and the voltage at the sensing electrode 314) may be used to determine the local power density (e.g. the power density adjacent to the ablation electrode 312). For example, the local power density may be determined by the Equation 1:

$$P_{loc} = I \Delta V \quad (1)$$

where $P_{loc}$ is the local power density, I is the current, and $\Delta V$ is the difference between the voltage at the ablation electrode 312 and the voltage at the sensing electrode 314. The local power density may then be used to adjust the power delivery of the system 300 to achieve the desired tissue modulation.

It is further contemplated that tissue impedance may be monitored during an ablation/sensing duty cycle which may be used alternate between ablation and impedance measurements. As ablation of the target region progresses, the impedance properties of the local tissue 306 may change thus changing the impedance calculated between the ablation electrode 312 and the contact ground pad 320 and/or between the ablation electrode 312 and the sensing electrode 314. It is contemplated that poor ground pad 320 contact may also be detected during the ablation process.

While not explicitly shown, the ablation electrode 312 may be connected to a control unit (such as control unit 18 in FIG. 1) by electrical conductors. Once the modulation system 300 has been advanced to the treatment region, energy may be supplied to the ablation electrode 312. The amount of energy delivered to the ablation electrode 312 may be determined by the desired treatment as well as the feedback obtained from the sensing electrodes 314. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 300 may monitor impedance values of the surrounding tissue 306 prior to beginning the ablation procedure and adjust the ablation parameters accordingly. It is further contemplated that other electrical properties of the local tissue 306 such as permittivity and/or conductivity may be used to set the current and/or power for RF or other sources of ablation energy to target tissues.

The modulation system 300 may be advanced through the vasculature in any manner known in the art. For example, system 300 may include a guidewire lumen to allow the system 300 to be advanced over a previously located guidewire. In some embodiments, the modulation system 300 may be advanced, or partially advanced, within a guide sheath such as the sheath 16 shown in FIG. 1. Once the ablation electrode 312 of the modulation system 300 has been placed adjacent to the desired treatment area, positioning mechanisms may be deployed, if so provided. For example, in some embodiments, the elongate shaft 308 may include push and/or pull wires to deflect a distal end region of the elongate shaft 308. For example, a push and/or pull wire may be attached adjacent to the distal end 310 of the elongate shaft 308 and then extend along an outer surface of the elongate shaft 308 or along an interior passageway formed in the shaft 308 to a position where it is accessible to a user. In other embodiments, the elongate shaft 308 may incorporate a planar deflection mechanism, such as a rib and spine mechanism. However, it is contemplated that the elongate shaft 308 may be deflected in any desired manner. The ablation electrode 312 and the sensing electrode 314 may be positioned adjacent to the deflectable region of the elongate shaft 308. Deflection of the elongate shaft 308 may position the ablation electrode 312 adjacent a first target region and the sensing electrode 314 adjacent a second target region.

As discussed above, the ablation electrode 312 and the sensing electrode 314 may be connected to a control unit (such as control unit 18 in FIG. 1) by insulated electrical conductors. Once the modulation system 300 has been advanced to the treatment region, energy may be supplied to the ablation electrode 312. As discussed above, the energy may be supplied to both the ablation electrode 312 and/or the sensing electrode 314 simultaneously or in an alternating duty cycle as desired. The amount of energy delivered to the ablation electrode 312 may be determined by the desired treatment as well as the feedback provided by the sensing electrode 314.

It is contemplated if an ablation electrode 312 is provided that does not extend around the entire circumference of the elongate shaft 308, the elongate shaft 308 may need to be circumferentially repositioned and energy may once again be delivered to the ablation electrode 312 to adequately ablate the target tissue. The number of times the elongate shaft 308 is rotated at a given longitudinal location may be determined by the number and size of the ablation electrode(s) 312 on the elongate shaft 308. Once a particular location has been ablated, it may be desirable to perform further ablation at different longitudinal locations. Once the elongate shaft 308 has been longitudinally repositioned, energy may once again be delivered to the ablation electrode 312. If necessary, the elongate shaft 308 may be circumferentially repositioned at each longitudinal location. This process may be repeated at any number of longitudinal locations desired. It is contemplated that in some embodiments, the system 300 may include ablation electrodes 312 at various positions along the length of the modulation system 300 such that a larger region may be treated without longitudinal displacement of the elongate shaft 308.

While FIG. 4 illustrates the ablation electrode 312 and the sensing electrode 314 in direct contact with the vessel wall, it is contemplated that the ablation electrode 312 and/or the sensing electrode 314 may be positioned away from the vessel wall 304 in an off-the-wall configuration. While not explicitly shown, the modulation system 300 may further include structure to maintain the ablation electrode 312 in the off-the-wall configuration. For example, in some instances the elongate shaft may further include a positioning basket configured to expand and engage the vessel wall 304 to center the electrode 312. In other embodiments elongate shaft 308 may further include a partially occlusive balloon which may be used to position the ablation electrode 312 and/or to increase the blood velocity near the ablation electrode 312 to provide better vessel wall cooling. It is contemplated that the elongate shaft 308 may further include an infusion lumen configured to perfuse the vessel lumen 302 with saline or other conductive fluid during the ablation procedure. In some instances, the perfused fluid may be provided at room temperature or cooler.

Figure 5:
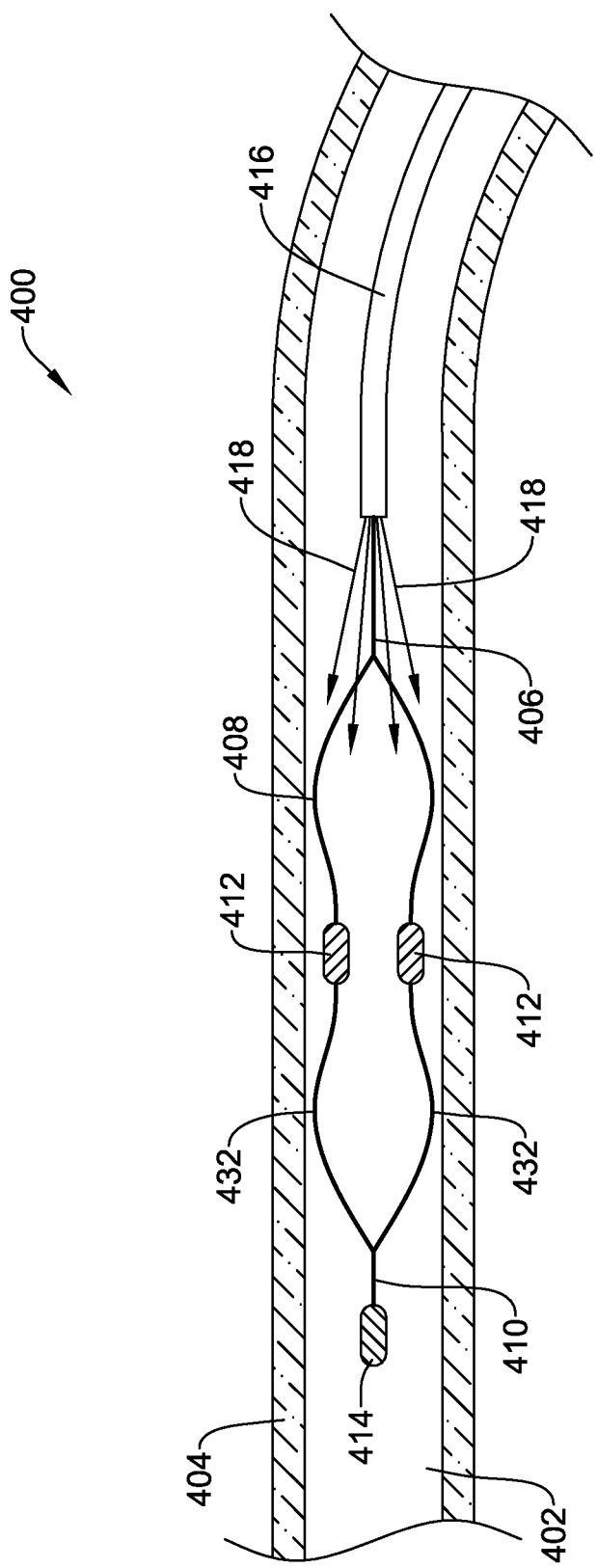
FIG. 5 illustrates a distal end of another illustrative renal nerve modulation system.

FIG. 5 is another illustrative embodiment of a distal end of a renal nerve modulation system 400 that may be similar in form and function to other systems disclosed herein. The modulation system 400 may be disposed within a body lumen 402 having a vessel wall 404. The vessel wall 404 may be surrounded by local target tissue. It may be desirable to determine local tissue impedance and monitor tissue changes in order to control energy delivery for proper target tissue ablation. The nerve modulation system 400 may include a high-impedance or low-impedance sensing electrode 414 to determine local impedance in the target tissue and surrounding blood. It is contemplated that tissue impedance may be monitored during RF, ultrasound, laser, microwave, or other ablation methods.

The system 400 may include an elongate member 406 having an expandable framework 408 disposed adjacent the distal end region 410. In some instances, the modulation system 400 may include an expandable balloon in place of the expandable framework 408. It is further contemplated that the modulation system 400 may not include an expandable portion. The elongate member 406 may extend proximally from the distal end region 410 to a proximal end configured to remain outside of a patient's body. The proximal end of the elongate member 406 may include a hub attached thereto for connecting other treatment devices or providing a port for facilitating other treatments. It is contemplated that the stiffness of the elongate member 406 may be modified to form modulation system 400 for use in various vessel diameters. In some instances, the elongate member 406 may be a wire having a generally solid cross-section. In other embodiments, the elongate member 406 may include one or more lumens extending therethrough. For example, the elongate member 406 may include a guide wire lumen and/or one or more auxiliary lumens. The lumens may be configured in any suitable way such as those ways commonly used for medical devices. While not explicitly shown, the modulation system 400 may further include temperature sensors/wires, an infusion lumen, radiopaque marker bands, fixed guidewire tip, external sheath and/or other components to facilitate the use and advancement of the system 400 within the vasculature.

The system 400 may further include one or more ablation electrodes 412 disposed on the expandable framework 408. The ablation electrodes 412 may be positioned on separate struts 432 of the expandable framework 408 such that the when the framework 408 is expanded the ablation electrodes 412 are positioned adjacent to opposite sides of the vessel wall 404. While the system 400 is illustrated as including two ablation electrodes 412, it is contemplated that the modulation system 400 may include any number of ablation electrodes 412 desired, such as, but not limited to, one, three, four, or more. If multiple ablation electrodes 412 are provided, the ablation electrodes 412 may be longitudinally and/or radially and/or circumferentially spaced as desired. In some instances, the ablation electrodes 412 may be positioned to be adjacent to opposite sides of the vessel 404. The ablation electrodes 412 may include similar features and may function in a similar manner to the ablation electrode discussed with respect to FIG. 2. In some embodiments, the ablation electrodes 412 may be positioned proximal of the distal end region 410 of the elongate member 406. In other embodiments, the ablation electrodes 412 may be positioned adjacent to the distal end region 410. It is further contemplated that the ablation electrodes 412 may function as both ablation and sensing electrodes.

The modulation system 400 may further include a sensing electrode 414. It is contemplated that the modulation system 400 may include more than one sensing electrode 414 to further refine the tissue evaluation. The sensing electrode 414 may include similar features and may function in a similar manner to the sensing electrode discussed with respect FIG. 2. In some instances, a high impedance sensing electrode 414 may be used in order to avoid significant distortion of the electric field and to avoid bipolar ablation between the ablation electrode 412 and the sensing electrode 414. In other instances, a low-impedance sensing electrode 414 may be used. In some embodiments, the sensing electrode 414 may be located distal of the ablation electrodes 412 and adjacent to the distal end region 410. In other embodiments, the sensing electrode 414 may be located proximal of the ablation electrodes 412.

The ablation electrodes 412 and the sensing electrode 414 may be used to monitor the impedance of the local tissue. While not explicitly shown, the ablation electrode 412 and the sensing electrode 414 may be connected through separate insulated conductors to a control unit (such as control unit 18 in FIG. 1). In some instances, the ablation electrodes 412 may be used as sensing electrodes to determine local tissue impedance. The ablation electrodes 412 may be spaced a distance from the sensing electrode 414 such that voltage applied to the electrodes 412, 414 may cause current to flow between the electrodes 412, 414 through the blood and nearby tissues. Measurement of the current may allow the resistance or complex impedance of the blood and tissue to be calculated. Various frequencies may be used to determine one or more impedance values, or a simpler calculation of resistance at low frequency can be utilized.

Figure 6:
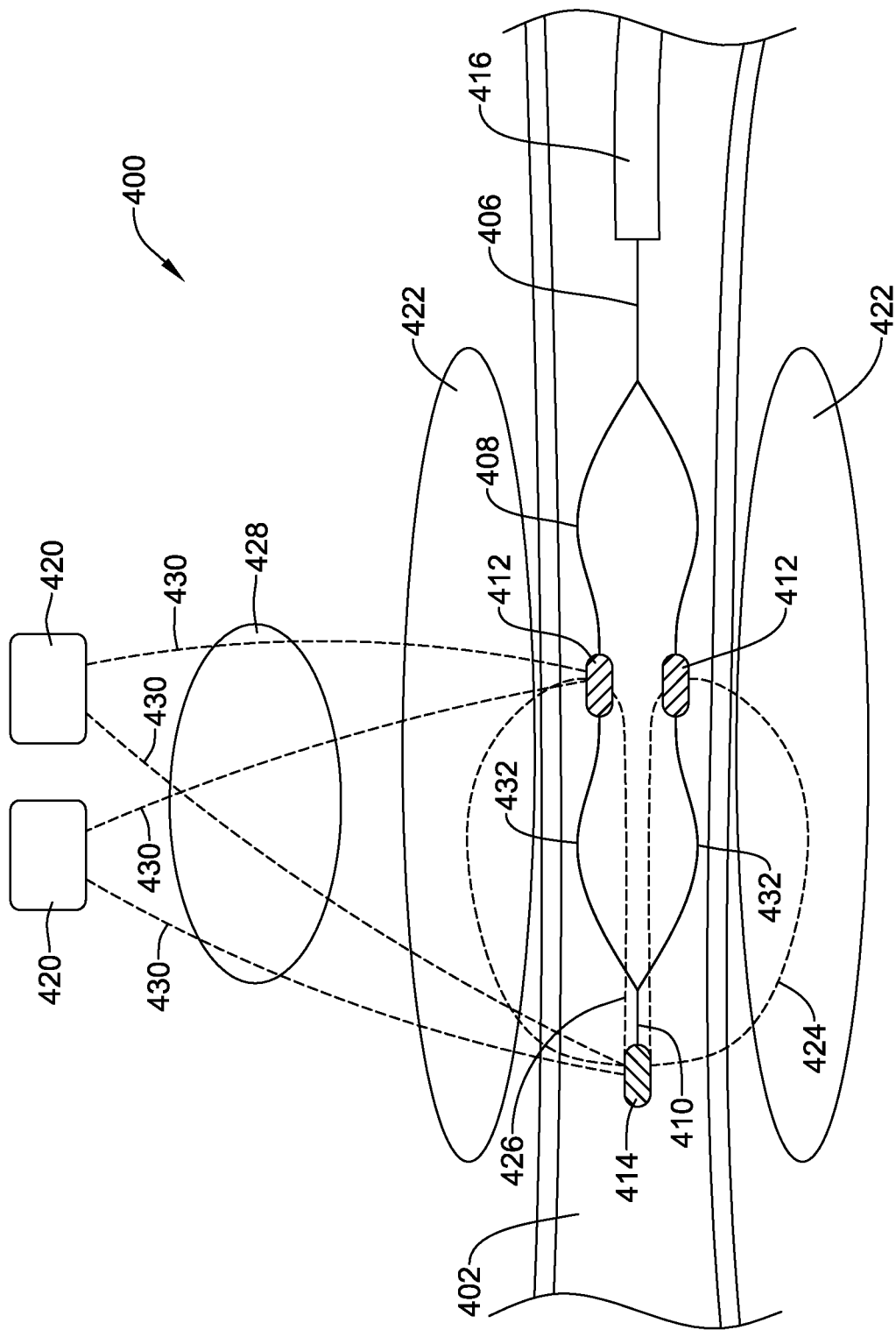
FIG. 6 is another illustrative view of the renal nerve modulation system of FIG. 5.

In some instances, it may be desirable to calculate the impedance of the blood or other fluid within the body lumen 402. The modulation system may include a catheter shaft 416 including a lumen for perfusing saline or other fluid 418 with known conductivity into the body lumen 402. In some instances, the perfused fluid 418 may be provided at room temperature or cooler. It is contemplated that multiple fluids and/or concentrations with known conductivity may be used. The impedance may be determined while the fluid 418 is being perfused. The difference between the impedance calculated with blood and the impedance calculated with the perfused fluid may be used to calculate the impedance of the blood. Referring to FIG. 6, which illustrates the current paths between various electrodes and ground pads, skin-contact ground pads 420 may also be connected through an electrical conductor to the control unit. As voltage is applied to the ablation electrodes 412, current 430 may pass through the local tissue 422 and additional body tissue 428 to the ground pads 420. Analysis of the impedance measurements between the ablation electrodes 412 and the sensing electrode 414 and between the ablation electrodes 412 and the ground pads 420 and/or between the sensing electrode 414 and the ground pads 420 may determine the tissue impedance in the local tissue 422 (e.g. target region) adjacent the electrodes 412, 414.

Tissue impedance may be monitored during simultaneous RF ablation (e.g. energy is applied simultaneously to the ablation electrode 412 and the sensing electrodes 414). In such a case, most of the current 430 may flow between the ablation electrode 412 and the skin-contact ground pads 420 and through the perivascular target tissues to be ablated, while a small amount of current 424, 426 may flow between the ablation electrodes 412 and the sensing electrode 414. As noted above, some of the current 424 will pass through the local tissue 422 while some of the current 426 will pass through the fluid in the body lumen 402 (e.g. blood or perfused fluid). The body impedance resulting from body tissue 428 outside of the local tissue 422 region between the ablation electrode 412 and skin contact ground pad 420 may also be measured. The impedance of the blood, local tissue 422, and body tissue 428 may be used to properly adjust the RF energy applied for ablation of the target tissue. It is further contemplated that impedance of the blood, local tissue 422, and body tissue 428 may be monitored during an ablation/sensing duty cycle which may be used alternate between ablation and impedance measurements. As ablation of the target region progresses, the impedance properties of the local tissue may change thus changing the impedance calculated between the ablation electrode 412 and the contact ground pad 420 and/or between the ablation electrodes 412 and the sensing electrode 414. Multiple measurements between the electrodes 412, 414 and/or the ground pads 420 (with blood or perfused fluid 418) may account for the location of the system 400 and vessel geometry effects. It is contemplated that poor ground pad 420 contact may also be detected during the ablation process.

While not explicitly shown, the ablation electrodes 412 may be connected to a control unit (such as control unit 18 in FIG. 1) by electrical conductors. Once the modulation system 400 has been advanced to the treatment region, energy may be supplied to the ablation electrodes 412. The amount of energy delivered to the ablation electrodes 412 may be determined by the desired treatment as well as the feedback obtained from the impedance calculations. It is contemplated that the impedance of the blood, local tissue 422, and body tissue 428 may be determined prior to and/or during the ablation procedure. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 400 may monitor impedance values of the surrounding tissue prior to beginning the ablation procedure and adjust the ablation parameters accordingly. It is further contemplated that other electrical properties of the local tissue such as permittivity and/or conductivity may be used to set the current and/or power for RF or other sources of ablation energy to target tissues.

The modulation system 400 may be advanced through the vasculature in any manner known in the art. For example, system 400 may include a guidewire lumen to allow the system 400 to be advanced over a previously located guidewire. In some embodiments, the modulation system 400 may be advanced, or partially advanced, within a guide sheath such as the sheath 16 shown in FIG. 1. Once the ablation electrodes 412 of the modulation system 400 have been placed adjacent to the desired treatment area, positioning mechanisms may be deployed, if so provided. For example, once the distal end region 410 has been placed adjacent to the target region, the catheter shaft 416 may be retracted and the framework 408 allowed to expand. It is contemplated that other known mechanisms may be used to deploy the framework 408. For example, a stent or expandable balloon may be used to expand the framework 408. It is further contemplated that the framework 408 may be formed of a shape-memory material, such as nitinol, such that additional structure is not necessary to expand the framework 408. Expansion of the framework 408 may place the ablation electrodes 412 adjacent to the desired treatment region.

As discussed above, the ablation electrodes 412 and the sensing electrode 414 may be connected to a control unit (such as control unit 18 in FIG. 1) by insulated electrical conductors. Once the modulation system 400 has been advanced to the treatment region, energy may be supplied to the ablation electrodes 412. As discussed above, the energy may be supplied to both the ablation electrodes 412 and/or the sensing electrode 414 simultaneously or in an alternating duty cycle as desired. The amount of energy delivered to the ablation electrodes 412 may be determined by the desired treatment as well as the feedback provided by the sensing electrode 414.

It is contemplated if an ablation electrode 412 is provided that does not extend around the entire circumference of the elongate member 406, the elongate member 406 may need to be circumferentially and/or radially repositioned and energy may once again be delivered to the ablation electrodes 412 to adequately ablate the target tissue. The number of times the elongate member 406 is repositioned at a given longitudinal location may be determined by the number and size of the ablation electrodes 412 on the elongate member 406. Once a particular location has been ablated, it may be desirable to perform further ablation at different longitudinal locations. Once the elongate member 406 has been longitudinally repositioned, energy may once again be delivered to the ablation electrodes 412. If necessary, the elongate member 406 may be radially repositioned at each longitudinal location. This process may be repeated at any number of longitudinal locations desired. It is contemplated that in some embodiments, the system 400 may include ablation electrodes 412 at various positions along the length of the modulation system 400 such that a larger region may be treated without longitudinal displacement of the elongate member 406.

While FIG. 5 illustrates the sensing electrodes 414 in an off-the-wall configuration, it is contemplated that the sensing electrodes 414 may be in direct contact with the vessel wall 404. As the sensing electrodes 414 may be operated at a frequency which does not result in tissue ablation, placing the sensing electrodes 414 against the vessel wall 404 will not cause vessel damage. In instances where direct contact ablation is acceptable, the ablation electrodes 412 may also be placed in contact with the vessel wall 404.

Figure 7:
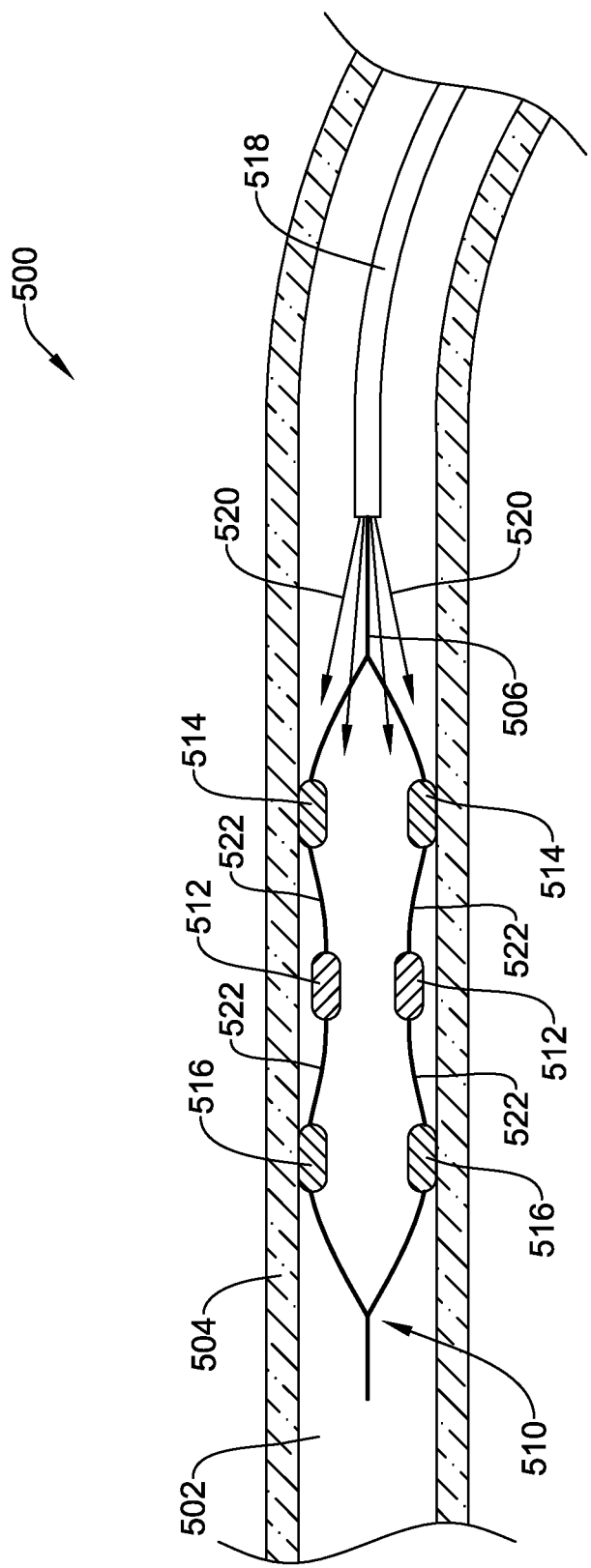
FIG. 7 illustrates a distal end of another illustrative renal nerve modulation system.

FIG. 7 is another illustrative embodiment of a distal end of a renal nerve modulation system 500 that may be similar in form and function to other systems disclosed herein. The modulation system 500 may be disposed within a body lumen 502 having a vessel wall 504. The vessel wall 504 may be surrounded by local target tissue. It may be desirable to determine local tissue impedance and monitor tissue changes in order to control energy delivery for proper target tissue ablation. The nerve modulation system 500 may include one or more high-impedance or low-impedance sensing electrodes 514, 516 to determine local impedance in the target tissue and surrounding blood. It is contemplated that tissue impedance may be monitored during unipolar or bipolar RF, ultrasound, laser, microwave, or other ablation methods.

The system 500 may include an elongate member 506 having an expandable framework 508 disposed adjacent the distal end region 510 may include similar features and may function in a similar manner to the expandable framework described with respect to FIG. 5. The elongate member 506 may extend proximally from the distal end region 510 to a proximal end configured to remain outside of a patient's body. The proximal end of the elongate member 506 may include a hub attached thereto for connecting other treatment devices or providing a port for facilitating other treatments. It is contemplated that the stiffness of the elongate member 506 may be modified to form modulation system 500 for use in various vessel diameters. In some instances, the elongate member 506 may be a wire having a generally solid cross-section. In other embodiments, the elongate member 506 may include one or more lumens extending therethrough. For example, the elongate member 506 may include a guide wire lumen and/or one or more auxiliary lumens. The lumens may be configured in any suitable way such as those ways commonly used for medical devices. While not explicitly shown, the modulation system 500 may further include temperature sensors/wires, an infusion lumen, radiopaque marker bands, fixed guidewire tip, external sheath and/or other components to facilitate the use and advancement of the system 500 within the vasculature.

The system 500 may further include one or more ablation electrodes 512 disposed on the expandable framework 508. The ablation electrodes 512 may be positioned on separate struts 522 of the expandable framework 508 such that the when the framework 508 is expanded the ablation electrodes 512 are positioned adjacent to opposite sides of the vessel wall 504. While the system 500 is illustrated as including two ablation electrodes 512, it is contemplated that the modulation system 500 may include any number of ablation electrodes 512 desired, such as, but not limited to, one, three, four, or more. If multiple ablation electrodes 512 are provided, the ablation electrodes 512 may be longitudinally and/or radially and/or circumferentially spaced as desired. In some instances, the ablation electrodes 512 may be positioned to be adjacent to opposite sides of the vessel 504. The ablation electrodes 512 may include similar features and may function in a similar manner to the ablation electrode discussed with respect to FIG. 2. In some embodiments, the ablation electrodes 512 may be positioned proximal of the distal end region 510 of the elongate member 506. In other embodiments, the ablation electrodes 512 may be positioned adjacent to the distal end region 510. It is further contemplated that the ablation electrodes 512 may function as both ablation and sensing electrodes.

The modulation system 500 may further include a pair of proximal sensing electrodes 514 and a pair of distal sensing electrodes 516. It is contemplated that the modulation system 500 may include fewer than or more than four sensing electrodes 514, 516 to further refine the tissue evaluation. The sensing electrodes 514, 516 may include similar features and may function in a similar manner to the sensing electrodes discussed with respect FIG. 2. In some instances, high-impedance sensing electrodes 514, 516 may be used in order to avoid significant distortion of the electric field and to avoid bipolar ablation between the ablation electrodes 512 and the sensing electrodes 514, 516. In other instances, low-impedance sensing electrodes 514, 516 may be used. The sensing electrodes 514, 516 may be symmetrically placed about the ablation electrodes 512 such that they can easily track the change which occurs to the tissue impedance in the ablation zone located between them. However, the sensing electrodes 514, 516 may be arranged in any orientation desired. The sensing electrodes 514, 516 may be in direct contact with the vessel wall 504. As the sensing electrode 414 may be operated at a frequency which does not result in tissue ablation, placing the sensing electrodes 514, 516 against the vessel wall 504 will not cause vessel damage. In instances where direct contact ablation is acceptable, the ablation electrodes 512 may also be placed in contact with the vessel wall 504. While FIG. 7 illustrates the sensing electrodes 514, 516 in direct contact with the vessel wall, it is contemplated that the sensing electrodes 514, 516 may be positioned away from the vessel wall 504 in an off-the-wall configuration.

The ablation electrodes 512 and the sensing electrodes 514, 516 may be used to monitor the impedance of the local tissue. While not explicitly shown, the ablation electrodes 512 and the sensing electrodes 514, 516 may be connected through separate insulated conductors to a control unit (such as control unit 18 in FIG. 1). The sensing electrodes 514, 516 may be spaced a distance from one another such that voltage applied to the sensing electrodes 514, 516 may cause current to flow between the sensing electrodes 514, 516 through the blood and nearby tissues. Measurement of the current may allow the resistance or complex impedance of the blood and tissue to be calculated. Various frequencies may be used to determine one or more impedance values, or a simpler calculation of resistance at low frequency can be utilized.

In some instances, it may be desirable to calculate the impedance of the blood or other fluid within the body lumen 502. The modulation system may include a catheter shaft 518 including a lumen for perfusing saline 520 or other fluid with known conductivity into the body lumen 502. In some instances, the perfused fluid 520 may be provided at room temperature or cooler. It is contemplated that multiple fluids and/or concentrations with known conductivity may be used. The impedance may be determined while the fluid 520 is being perfused. The difference between the impedance calculated with blood and the impedance calculated with the perfused fluid may be used to calculate the impedance of the blood.

While not explicitly shown, skin-contact ground pads may also be connected through an electrical conductor to the control unit. As voltage is applied to the ablation electrodes 512, current may pass through the local tissue and additional body tissue to the ground pads. Analysis of the impedance measurements between the ablation electrodes 512 and the sensing electrodes 514, 516 and between the ablation electrodes 512 and the ground pads and/or between the sensing electrodes 514, 516 and the ground pads may determine the tissue impedance in the local tissue (e.g. target region) adjacent the electrodes 512, 514, 516.

Tissue impedance may be monitored during simultaneous RF ablation (e.g. energy is applied simultaneously to the ablation electrodes 512 and the sensing electrodes 514, 516) or during an ablation/sensing duty cycle which may be used alternate between ablation and impedance measurements. The tissue impedance may be determined in a similar manner to that discussed with respect to other modulation systems described herein. As ablation of the target region progresses, the impedance properties of the local tissue may change thus changing the impedance calculated between the ablation electrodes 512 and the contact ground pad and/or between the ablation electrodes 512 and the sensing electrodes 514, 516. Multiple measurements between the electrodes 512, 514, 516 and/or the ground pads (with blood or perfused fluid 520) may account for the location of the system 500 and vessel geometry effects. It is contemplated that poor ground pad contact may also be detected during the ablation process.

While not explicitly shown, the ablation electrodes 512 may be connected to a control unit (such as control unit 18 in FIG. 1) by electrical conductors. Once the modulation system 500 has been advanced to the treatment region, energy may be supplied to the ablation electrodes 512. The amount of energy delivered to the ablation electrodes 512 may be determined by the desired treatment as well as the feedback obtained from the impedance calculations. It is contemplated that the impedance of the blood, local tissue, and body tissue may be determined prior to and/or during the ablation procedure. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 500 may monitor impedance values of the surrounding tissue prior to beginning the ablation procedure and adjust the ablation parameters accordingly. It is further contemplated that other electrical properties of the local tissue such as permittivity and/or conductivity may be used to set the current and/or power for RF or other sources of ablation energy to target tissues.

The modulation system 500 may be advanced through the vasculature in any manner known in the art such, but not limited to, those methods discussed with respect to other modulation systems described herein. Once the ablation electrodes 512 of the modulation system 500 have been placed adjacent to the desired treatment area, positioning mechanisms may be deployed, if so provided. For example, once the distal end region 510 has been placed adjacent to the target region, the catheter shaft 518 may be retracted and the framework 508 allowed to expand in similar manners to those discussed with respect to modulation system 400.

As discussed above, the ablation electrodes 512 and the sensing electrodes 514, 516 may be connected to a control unit (such as control unit 18 in FIG. 1) by insulated electrical conductors. Once the modulation system 500 has been advanced to the treatment region, energy may be supplied to the ablation electrodes 512. As discussed above, the energy may be supplied to both the ablation electrodes 512 and/or the sensing electrodes 514, 516 simultaneously or in an alternating duty cycle as desired. The amount of energy delivered to the ablation electrodes 512 may be determined by the desired treatment as well as the feedback provided by the sensing electrodes 514, 516. The modulation system 500 may be radially, longitudinally, and/or circumferentially repositioned and energy subsequently applied as many times as necessary to complete the desired ablation. The number of times the modulation system 500 is repositioned may be determined by the number and size of the ablation electrodes 512 on the elongate member 506.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method for detecting tissue changes during tissue modulation in a patient, the method comprising:
    inserting a tissue modulation system into a lumen in the patient, the tissue modulation system comprising:
        an elongate shaft having a proximal end region and a distal end region;
        at least two electrodes disposed adjacent to the distal end region, a first electrode of the at least two electrodes spaced a distance from a second electrode of the at least two electrodes;
    advancing the tissue modulation system through the lumen such that the distal end region is adjacent to a target region within the patient while the proximal end region remains outside the patient;
    applying a voltage to the modulation system to impart a current between the first and second electrodes;
    calculating an impedance of the target region from the current;
    applying a voltage to at least one of the first or second electrodes to effect tissue modulation on the target region; and
    monitoring the current between the first and second electrodes for changes in the impedance of the target region.

2. The method of claim 1, wherein the impedance of the target region is calculated before effecting tissue modulation on the target region.

3. The method of claim 1, wherein monitoring the current between the first and second electrodes for changes in the impedance of the target region is performed simultaneously with the tissue modulation.

4. The method of claim 1 wherein monitoring the current between the first and second electrodes for changes in the impedance of the target region and the tissue modulation are performed alternately.

5. The method of claim 1, wherein the amount of voltage applied to at least one of the first or second electrodes to effect tissue modulation on the target region is determined at least in part by the calculated impedance of the target region.

6. The method of claim 1, further comprising withdrawing the tissue modulation system from the patient.

7. The method of claim 1, wherein the tissue modulation includes ablation.

8. A method for detecting tissue changes during tissue ablation, the method comprising:
    advancing a tissue ablation system through a lumen such that a distal end region thereof is adjacent to a target region, the tissue ablation system comprising:
        an elongate shaft having a proximal end region and a distal end region;
        at least two electrodes disposed adjacent to the distal end region, a first electrode of the at least two electrodes spaced a distance from a second electrode of the at least two electrodes;
    applying a voltage to the ablation system to impart a current between the first and second electrodes;
    calculating an impedance of the target region from the current; and
    applying a voltage to at least one of the first or second electrodes to effect tissue ablation on the target region; and
    monitoring the current between the first and second electrodes for changes in the impedance of the target region.

9. The method of claim 8, wherein the impedance of the target region is calculated before effecting tissue ablation on the target region.

10. The method of claim 8, wherein monitoring the current between the first and second electrodes for changes in the impedance of the target region is performed simultaneously with the tissue ablation.

11. The method of claim 8 wherein monitoring the current between the first and second electrodes for changes in the impedance of the target region and the tissue ablation are performed alternately.

12. The method of claim 8, wherein the amount of voltage applied to at least one of the first or second electrodes to effect tissue ablation on the target region is determined at least in part by the calculated impedance of the target region.

13. The method of claim 8, further comprising removing the tissue ablation system from the lumen.

14. The method of claim 8, wherein advancing the tissue ablation system through a lumen includes positioning the distal end region of the tissue ablation system adjacent the target region within a patient while maintaining the proximal end region of the elongate shaft outside the patient.

* * * * *